(12) United States Patent
Biedermann et al.

(10) Patent No.: US 8,603,173 B2
(45) Date of Patent: *Dec. 10, 2013

(54) SPACE KEEPER WITH ADJUSTABLE AXIAL LENGTH

(75) Inventors: Lutz Biedermann, VS-Villingen (DE); Jürgen Harms, Karlsruhe (DE); Peter Ostermann, Bocholt (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 463 days.

This patent is subject to a terminal disclaimer.

(21) Appl. No.: 12/414,624

(22) Filed: Mar. 30, 2009

(65) Prior Publication Data

US 2009/0276050 A1     Nov. 5, 2009

Related U.S. Application Data

(63) Continuation of application No. 10/250,489, filed as application No. PCT/EP02/08648 on Aug. 2, 2002, now Pat. No. 7,547,325.

(30) Foreign Application Priority Data

Aug. 3, 2001   (DE) ................................ 101 38 079

(51) Int. Cl.
*A61F 2/44* (2006.01)
(52) U.S. Cl.
USPC ...................................................... 623/17.16
(58) Field of Classification Search
USPC ............... 623/17.11–17.16, 23.45–23.47; 403/43–48, 109.1–109.4, 238, 377, 403/378, 379.3
See application file for complete search history.

(56) References Cited

U.S. PATENT DOCUMENTS

| 661,620 | A | * | 11/1900 | Rumbarger | ................... 403/290 |
| 2,678,226 | A | | 5/1954 | Wright | |
| 4,553,273 | A | | 11/1985 | Wu | |
| 4,599,086 | A | * | 7/1986 | Doty | ........................... 606/86 A |
| 5,571,192 | A | * | 11/1996 | Schonhoffer | .............. 623/17.11 |
| 5,702,455 | A | | 12/1997 | Saggar | |
| 5,776,198 | A | * | 7/1998 | Rabbe et al. | ............... 623/17.15 |
| 6,200,348 | B1 | | 3/2001 | Biedermann et al. | |
| 6,454,806 | B1 | | 9/2002 | Cohen et al. | |
| 6,719,796 | B2 | | 4/2004 | Cohen et al. | |

FOREIGN PATENT DOCUMENTS

| EP | 0 977 528 | | 2/2000 |
| EP | 1 080 703 | A2 | 3/2001 |
| WO | WO 95/25485 | | 9/1995 |
| WO | WO 99/39665 | | 8/1999 |
| WO | WO 99/63913 | | 12/1999 |

* cited by examiner

*Primary Examiner* — Anu Ramana
(74) *Attorney, Agent, or Firm* — Christie, Parker & Hale, LLP

(57) ABSTRACT

A space keeper for insertion between two vertebrae which has a variable axial length is provided. The space keeper possesses a sleeve-like first member (2) and a second member (3) guided in the latter and movable relative to the first member in the axial direction for adjusting an overall length. In order that adjustability during operating is facilitated the two members (2, 3) are connected to one another by a lever (7, 8), wherein one center of motion (16) of the lever is connected to one member (3) and the other center of motion (18) is connected in terms of action to the other member (2).

9 Claims, 3 Drawing Sheets

SPACE KEEPER WITH ADJUSTABLE AXIAL LENGTH

CROSS-REFERENCE TO RELATED APPLICATION(S)

This application is a continuation of U.S. patent application Ser. No. 10/250,489, filed Jul. 2, 2003, now issued U.S. Pat. No. 7,547,325 issued Jun. 16, 2009, which is a 371 of PCT/EP02/08648, filed Aug. 2, 2002, the disclosures of which are incorporated fully herein by reference.

BACKGROUND OF THE INVENTION

The invention relates to a space keeper for inserting between two vertebrae, the space keeper having an adjustable axial length and a sleeve-like first member and a second member guided in the latter and movable in the axial direction relative to the first member for setting an overall length.

A space keeper of this type is known from EP 0 977 528 A1. In this the two members in the telescoped position are inserted between two vertebrae and then pulled apart by hand to the desired length and then locked in the extended position.

SUMMARY OF THE INVENTION

It is the object of the invention to provide a space keeper of the type described at the outset in which the operating surgeon can manage the adjustment to the desired length in the most simple manner.

This task is solved by a space keeper of the type described at the outset which is characterized in that the two members are connected to one another by a lever one of whose centers of motion is connected to one member and whose other centre of motion is connected to the other member.

Refinements of the invention are identified in the subsidiary claims.

Further features and functions of the invention emerge from the description of embodiments with reference to the figures. In the figures:

DETAILED DESCRIPTION OF THE INVENTION

Figure 1:
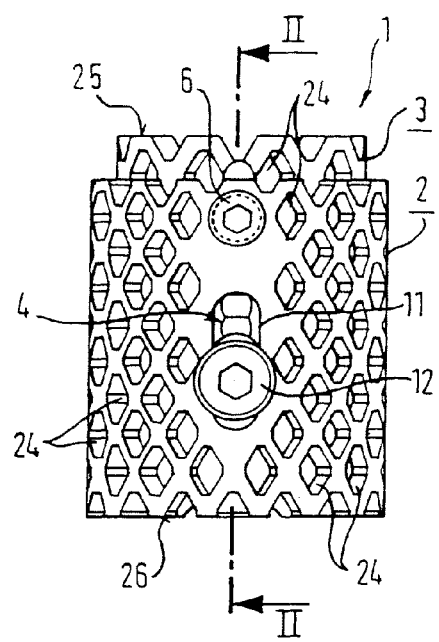
FIG. 1 a side view of the space keeper in the contracted position.

As may be seen best in FIG. 1 a space keeper 1 comprises a sleeve-like first member 2 and a sleeve-like second member 3 guided in the former. The two members can be pushed into one another to a maximum extent as shown in FIGS. 1 and 2 and be moved apart to a maximum length as shown in FIG. 3.

Figure 2:
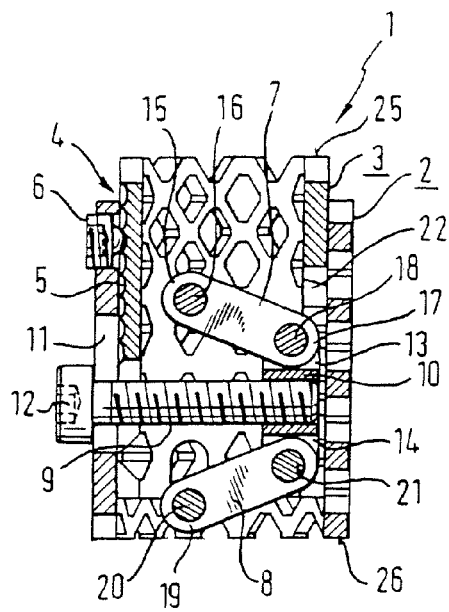
FIG. 2 a section along the line II/II in FIG. 1.
Figure 3:
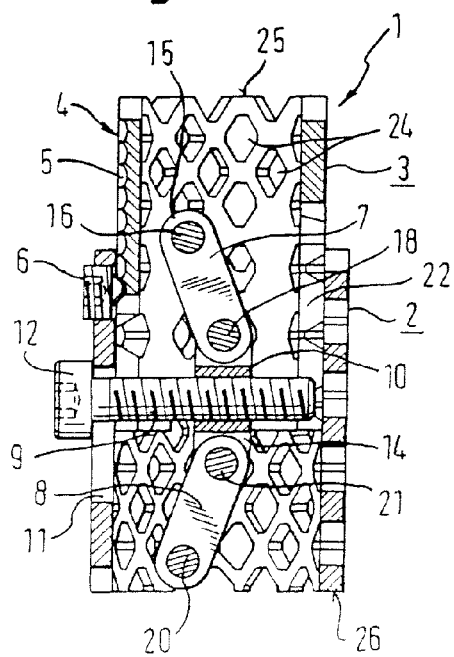
FIG. 3 the same section as in FIG. 2 but this time with the space keeper pulled apart to its maximum length.

As may be seen in FIGS. 1 to 3 the inner second member 3 has on its outer wall facing towards the outer first member 2 a section with a catch 4 extending in the axial direction having a plurality of depressions 5 arranged adjacent to one another in the axial direction and bounding one another and the outer first member 2 has a fixing member 6 which can be brought into engagement with the catch. The fixing member serves the purpose of locking the two members in a desired position.

Figure 4:
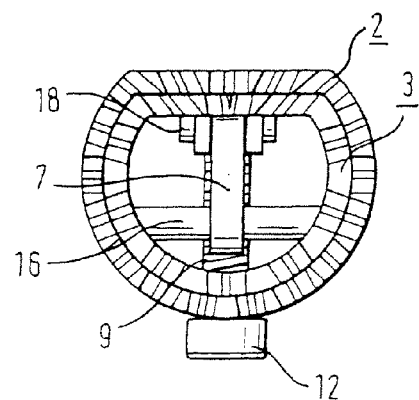
FIG. 4 a plan view onto the object shown in FIG. 1.

As may be seen best in FIGS. 2 and 4 the spacer 1 has a lever device for adjusting the axial position of the two members relative to one another. In the first embodiment this comprises a first lever arm 7, a second lever arm 8, a setting screw 9 and a threaded sleeve 10. As may be seen best in FIG. 2 the outer first member 2 has a recess 11 on the side whose lateral extension is smaller than the diameter of the head 12 of the setting screw 9 as may be seen best in FIG. 1. The setting screw 9 is inserted in the manner shown in FIG. 2 into the interior of the sleeve-like members at right angles to the axial direction. The threaded sleeve 10 is screwed onto the screw. On both sides extending in the axial direction of the sleeve it has shoulders 13, 14. The shoulder 13 serves to connect to the first lever arm 7. The lever arm is mounted pivotably about a shaft 16 by its first end 15 by means of this shaft mounted on two opposite points of the wall of the second member 3. The shaft extends perpendicular to the longitudinal axis of the space keeper. At its second end 17 opposite the connection to the shaft 16 the first lever arm is connected pivotably about a shaft 18 to the shoulder 13 via a pin or shaft 18. The pin or shaft 18 extends parallel to the shaft 16.

As illustrated in FIG. 2 the second lever arm 8 viewed about the setting screw 9 is constructed or arranged symmetrically relative to the first lever arm 7. At its first end 19 correspondingly located opposite end 15 the lever arm is mounted via a shaft 20 to pivot about the latter. The shaft 20 is mounted on the side in the side walls located opposite one another of the first member 2 and extends parallel to the shaft 16. At its end located opposite the end 19 the second lever arm is connected pivotably about a shaft 21 to the shoulder 14 by means of a pin or shaft 21.

As may be seen in FIGS. 1 and 2 the recess 11 is constructed as an oblong hole extending in a direction parallel to the longitudinal axis of the spacer. The oblong hole is positioned in such a way that the setting screw 9 is movable back and forth therein to such an extent that the screw is movable back and forth in the oblong hole from the compressed position shown in FIG. 2 to the extended position shown in FIG. 3.

In operation the space keeper in the contracted position shown in FIG. 2 with minimal length in the axial direction is inserted between the vertebrae. The length is then set to a desired length by engaging by means of a screwdriver in a corresponding slit or hexagonal opening of the head 12 of the setting screw 9 in that the setting screw 9 is turned in such a way that the threaded sleeve 10 is moved from the most extreme position shown in FIG. 2, in which the threaded sleeve is located at the free end of the setting screw 9, towards the head. In doing so the two levers 7, 8 are moved from their retracted position into a maximum extended position shown in FIG. 3. In this way the two sleeve-like members 2 and 3 are moved from the contracted position shown in FIG. 2 into the expanded position shown in FIG. 3 or any intermediate position. Due to the screw guidance between the setting screw 9 and threaded sleeve 10 the two members remain initially in the position reached by turning the setting screw 9. As soon as this position is regarded as final complete locking ensues by tightening the locking screw forming the fixing member 6 which for this purpose engages in a depression 5 of the catch 4.

In the embodiment described above the length of the setting screw 9 is chosen so that the setting screw reaches by its free end into the hollow interior of the second member 3 without coming into engagement with the opposite wall of the second member 3 so that there is no hindrance to the movement of the second member 3. As shown in the figures the second member 3 preferably has a recess 22 constructed in the form of an oblong hole which extends in its longitudinal direction parallel to the longitudinal axis of the space keeper and whose length and width are so constructed that the free end of the setting screw 9 with the threaded sleeve sliding thereon and the two shoulders 13 and 14 and the ends of the two lever arms 7 and 8 connected thereto in the back-and-forth movement shown in FIGS. 2 and 3 can move freely back and forth in the oblong hole. In this way it is achieved that the setting screw 9 may have a greater length by which means the travel of the threaded sleeve 10 is increased and hence the expandability of the two members or the space keeper is increased.

Figure 5:
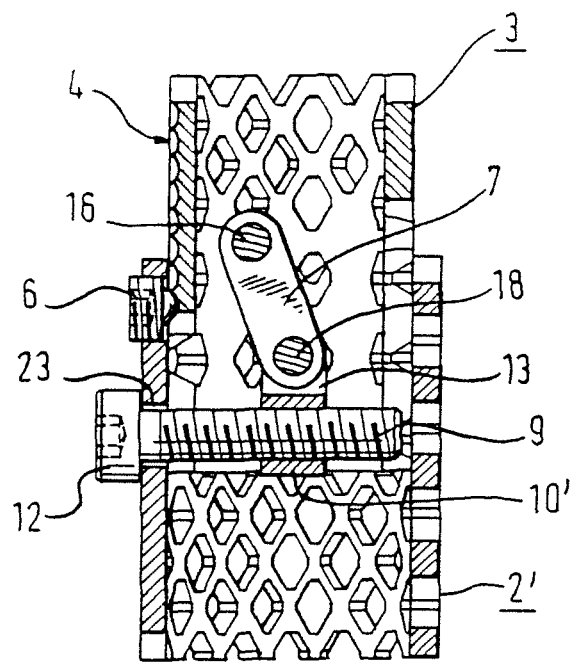
FIG. 5 a second embodiment in the extended position corresponding to the sectional illustration II/II.
Figure 6:
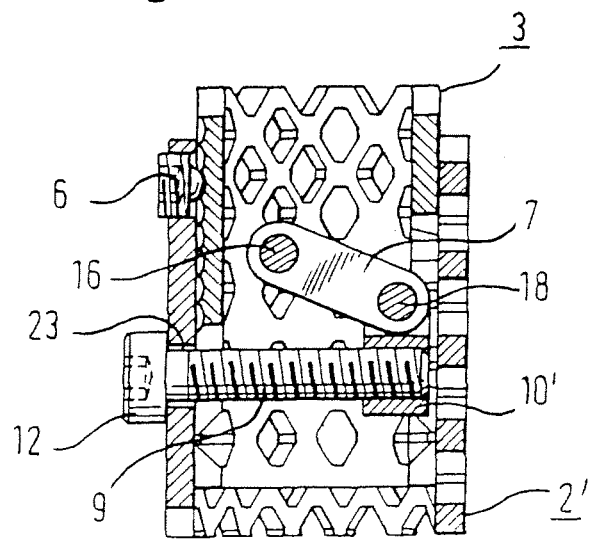
FIG. 6 the second embodiment in the contracted position.

In a modified embodiment shown in FIGS. 5 and 6 the second member 3, the setting screw 9, the first lever arm 7, the shoulder 13 and the two shafts 16 and 18 are constructed in the same way as the corresponding elements in the first embodiment.

In the second embodiment, instead of the oblong hole 11 a round hole 23 guiding the setting screw in the wall of the first member 2' is provided whose diameter is chosen so that the setting screw is guided rotatably in this hole. The threaded sleeve 10' has only one shoulder 13.

In operation adjustment between the compressed position shown in FIG. 6 and the expanded position shown in FIG. 5 is done as in the first embodiment by turning the setting screw 9 in such a way that the threaded sleeve 10' is screwed so far out of the most extreme position at the free end shown in FIG. 6 towards the head until expansion to a desired size has occurred or the lever 7 has moved almost into the vertical position. The concluding locking is done as in the first embodiment by tightening a fixing screw 6 in cooperation with the depressions 5 of the catch 4.

As may be seen in the figures the two walls of the first and second members are each constructed in such a way that they exhibit in the circumferential direction a plurality of diamond-shaped apertures 24. The free ends 25, 26 located opposite one another are as shown in the figures each of serrated construction whereby engagement in the adjoining vertebrae walls stabilizing against rotation is facilitated. The apertures in the wall facilitate ingrowing after the operation.

Figure 7:
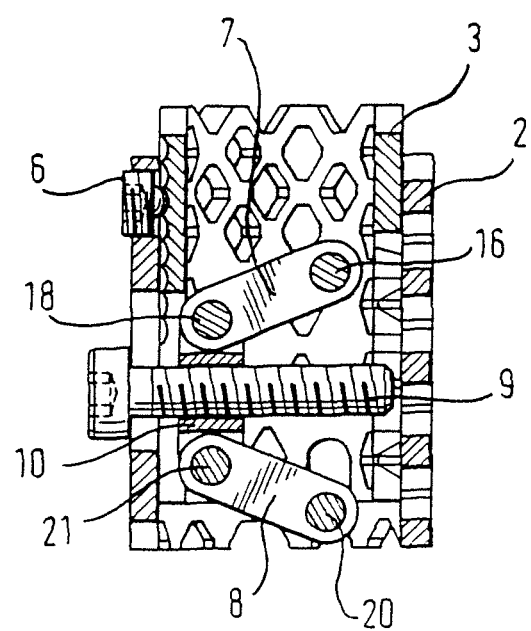
FIG. 7 a section through another embodiment.

In the embodiments described above the adjusting device of the setting screw 9, threaded sleeve 10 and lever arms 7, 8 or 7 is constructed in each case in such a way that the maximum extension occurs when the threaded sleeve 10 is moved to the maximum towards the head 12 and compressed to the furthest possible when the threaded sleeve 10 is at its greatest possible distance from the head 12. It is also possible, however, to reverse this device to the effect that the greatest extension possible is reached when the threaded sleeve 10 is at its greatest distance from the head 12. At the smallest distance from the head 12 the height has its lowest possible value. Such an embodiment is described in FIG. 7.

What is claimed is:

1. A space keeper for insertion between two vertebrae, comprising:
    a sleeve-like member having a longitudinal axis, a circumferential wall extending around the longitudinal axis and defining an interior space, and a free end at one end of the circumferential wall of the sleeve-like member to engage a first vertebra;
    an inner member guided in the interior space of the sleeve-like member and having a free end extending out of the sleeve-like member at an end of the space keeper opposite from the free end of the sleeve-like member to engage a second vertebra, the inner member movable in the interior space in the direction of the longitudinal axis relative to the sleeve-like member for setting an overall length of the space keeper from the free end of the sleeve-like member to the free end of the inner member;
    a lever in the interior space of the sleeve-like member, the lever pivotably connected to the sleeve-like member and the inner member; and
    a driver connectable to the lever to move the lever between a first position wherein a longitudinal axis of the lever is transverse to the longitudinal axis of the sleeve-like member and a second position wherein the longitudinal axis of the lever is closer to a position in which the longitudinal axis of the lever is parallel to the longitudinal axis of the sleeve-like member than in the first position;
    wherein the overall length of the space keeper is greater in one of the first and second positions than in the other of the first and second positions.

2. The space keeper according to claim 1, wherein the lever has two arms driven by the driver, one arm is pivotably connected to the sleeve-like member by a first shaft defining a first pivot axis and the other arm is pivotably connected to the inner member by a second shaft defining a second pivot axis that is spaced from the first pivot axis.

3. The space keeper according to claim 1, wherein the lever is of single-arm construction, wherein the one arm of the single-arm construction has two ends, one of the two ends is pivotably connected to the inner member by a first shaft defining a first pivot axis and the other of the two ends is connected to the driver by a second shaft defining a second pivot axis that is spaced from the first pivot axis.

4. The space keeper according to claim 1, wherein the driver engages the circumferential wall of the sleeve-like member and extends into the interior space of the sleeve-like member, and the inner member has a slot extending in a direction parallel to the longitudinal axis of the sleeve-like member into which slot the driver projects.

5. The space keeper according to claim 1, wherein the circumferential wall of the sleeve-like member has apertures through the wall and into the interior space.

6. The space keeper according to claim 1, wherein the inner member is a sleeve-like member having a circumferential wall defining an interior space, and the free end of the inner member is at one end of the circumferential wall of the inner member.

7. The space keeper according to claim 6, wherein the circumferential wall of the inner member has apertures that extend from an inner surface to an outer surface of the circumferential wall.

8. The space keeper according to claim 1, wherein the circumferential wall of the sleeve-like member defines an opening into the interior space of the sleeve-like member at its free end.

9. The space keeper according to claim 1, wherein the free ends of the sleeve-like member and the inner member have a serrated construction comprising spaced apart end surfaces to engage respective vertebrae for stabilizing the space keeper against rotation.

* * * * *

UNITED STATES PATENT AND TRADEMARK OFFICE
CERTIFICATE OF CORRECTION

PATENT NO. : 8,603,173 B2
APPLICATION NO. : 12/414624
DATED : December 10, 2013
INVENTOR(S) : Biedermann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this
Twelfth Day of May, 2015

Michelle K. Lee
*Director of the United States Patent and Trademark Office*